(12) United States Patent
Zhang

(10) Patent No.: US 12,184,976 B2
(45) Date of Patent: Dec. 31, 2024

(54) OPTICAL IMAGE STABILIZATION METHOD AND SYSTEM BASED ON LINE SCAN OPHTHALMOSCOPE IMAGING SYSTEM

(71) Applicant: ROBOTRAK TECHNOLOGIES CO., LTD., Nanjing (CN)

(72) Inventor: Jie Zhang, Nanjing (CN)

(73) Assignee: ROBOTRAK TECHNOLOGIES CO., LTD., Nanjing (CN)

( * ) Notice: Subject to any disclaimer, the term of this patent is extended or adjusted under 35 U.S.C. 154(b) by 537 days.

(21) Appl. No.: 17/606,312

(22) PCT Filed: May 5, 2019

(86) PCT No.: PCT/CN2019/085501
§ 371 (c)(1),
(2) Date: Oct. 25, 2021

(87) PCT Pub. No.: WO2020/215360
PCT Pub. Date: Oct. 29, 2020

(65) Prior Publication Data
US 2022/0217277 A1      Jul. 7, 2022

(30) Foreign Application Priority Data
Apr. 25, 2019   (CN) .................. 201910339894.X

(51) Int. Cl.
*A61B 3/10*  (2006.01)
*A61B 3/12*  (2006.01)
(Continued)

(52) U.S. Cl.
CPC ......... *H04N 23/6812* (2023.01); *A61B 3/102* (2013.01); *A61B 3/12* (2013.01); *A61B 3/14* (2013.01)

(58) Field of Classification Search
CPC ...... H04N 23/6812; A61B 3/102; A61B 3/12; A61B 3/14; A61B 3/113; A61B 3/1025
See application file for complete search history.

(56) References Cited

U.S. PATENT DOCUMENTS

| 2012/0128222 A1* | 5/2012 | Everett | ................ A61B 3/113 382/131 |
| 2017/0265742 A1* | 9/2017 | Nozato | ................ A61B 3/152 |

FOREIGN PATENT DOCUMENTS

| CN | 101072534 A | 11/2007 |
| CN | 108371542 A | 8/2018 |

(Continued)

OTHER PUBLICATIONS

International Search Report with English Translation for PCT Application No. PCT/CN2019/085501, Date of mailing Dec. 13, 2019, 5 pages.

*Primary Examiner* — Tuyen Tra
(74) *Attorney, Agent, or Firm* — Bayes PLLC

(57) ABSTRACT

Disclosed are an image stabilization method and system based on a line scan ophthalmoscope imaging system. The image stabilization system comprises a primary ophthalmoscope (LSO) imaging system with internal optical closed-loop tracking and an integrated auxiliary imaging system controlled by an LSO, wherein the primary LSO imaging system is used for performing imaging itself and providing fundus positioning and navigation for the auxiliary imaging system, and for calculating fundus or eyeball movement information obtained from an LSO image and performing closed-loop optical tracking; the auxiliary imaging system makes light emitted by a point light source reach an orthogonal scanning mirror via a collimation system and then be focused on a dichroic mirror (DM); and a corresponding spatial position of the orthogonal scanning mirror is adjusted in real time, so as to acquire a tomographic image of a (Continued)

required fundus position or realize fundus single-point or array target hitting.

12 Claims, 6 Drawing Sheets

(51) Int. Cl.
*A61B 3/14* (2006.01)
*H04N 23/68* (2023.01)

(56) References Cited

FOREIGN PATENT DOCUMENTS

| | | |
|---|---|---|
| CN | 108567410 A | 9/2018 |
| CN | 109330558 A | 2/2019 |

* cited by examiner (A)　　　　　(B)　　　　　(C)

(A)          (B)

OPTICAL IMAGE STABILIZATION METHOD AND SYSTEM BASED ON LINE SCAN OPHTHALMOSCOPE IMAGING SYSTEM

CROSS-REFERENCE TO RELATED APPLICATIONS

This application is the U.S. National Phase of PCT/CN2019/085501 filed May 5, 2019, which claims priority to Chinese Application No. 201910339894.X filed Apr. 25, 2019, the entire disclosures of which are incorporated by reference herein.

FIELD OF THE INVENTION

The present invention relates to laser fundus target tracking and imaging technology, and in particular to a method and system for optical image stabilization based on a line scan imaging system.

BACKGROUND

The existing target tracking technology based on a Line Scan Ophthalmoscope (LSO) imaging system, such as the Carl Zeiss imaging system, uses one frame of image as a unit to calculate a fundus target motion amount. However, there is a defect that the control system has a time delay of at least one frame, which may result in a decrease in tracking precision. Moreover, the existing LSO target tracking signal manner is completely digital. When extracting a signal from the image, due to lack of an optical closed-loop control measure inside the LSO, it may result in that a calculation of the fundus motion signal is likely not reliable.

SUMMARY OF THE INVENTION

In view of this, a main objective of the present invention is to provide a method and system for optical image stabilization based on a line scan imaging system (LSO), which aims to overcome the inherent optical and control defects of the existing LSO system and greatly improve its stability, accuracy and imaging efficiency in clinical application.

To achieve the above objective, the technical solution of the present invention is as follows.

An image stabilization system based on a line scan imaging system, including a primary (LSO) imaging system with an internal closed-loop optical tracking device and an integrated auxiliary imaging system controlled by the LSO;

the primary LSO imaging system is used for self-imaging and provides fundus positioning and navigation for the auxiliary imaging system, and calculates fundus or eyeball motion information obtained from the LSO image by executing a preset closed-loop control algorithm to perform closed-loop optical tracking;

the auxiliary imaging system passes the light emitted by the point light source through a collimating system to an orthogonal scanning mirror, then focuses the light on the dichroic mirror DM through the focusing lens, the DM is located on the focal plane of the primary LSO imaging system; by applying the closed-loop fundus or eyeball motion information to the orthogonal scanning mirrors of the auxiliary imaging system, corresponding spatial positions of the orthogonal scanning mirrors are adjusted in real time to obtain a tomographic image of the required fundus position or a fundus single point or array strike target.

Among them, the closed-loop optical tracking device of the primary LSO imaging system includes a second scanning mirror SM11, a first scanning mirror SM12 and a cylinder lens L13, which is used to calculate the fundus or eyeball motion information obtained from the LSO image, that is, the control signal, according to the preset closed-loop control algorithm, to realize the closed-loop optical tracking function.

The closed-loop optical tracking device of the primary LSO imaging system further comprises a rotating bracket of the line scan camera.

The auxiliary imaging system is an auxiliary optical coherence tomography OCT imaging system, or a fundus single point or array target strike imaging system.

The auxiliary imaging system further comprises a point light source, and the light emitted by the point light source passes through a collimating system composed of collimating lenses before reaching the orthogonal scanning mirror.

The primary LSO imaging system through the primary LSO image applies a cross-correlation algorithm to obtain the closed-loop fundus or eyeball motion position information $(x, y, \theta)$, input the closed-loop fundus or eyeball motion position information $(x, y, \theta)$ into the auxiliary imaging system, and lock the fundus target by adjusting the optical scanning position of the scanning mirror in real time; where $(x, y)$ is a translation amount of fundus motion, and $\theta$ is a rotation amount.

Preferably, the image stabilization system supports simultaneous implementation of two-dimensional fundus reflection imaging, two-dimensional fundus fluorescence imaging, three-dimensional OCT tomographic imaging, or fundus single point or array target strike imaging.

An image stabilization method based on a line scan imaging system, including the following steps:

A. adding an integrated auxiliary imaging system controlled by a primary LSO imaging system with internal closed-loop optical tracking to the primary LSO imaging system;

B. using the auxiliary imaging system, passing the light emitted by the point light source through a collimating system to an orthogonal scanning mirror, then focusing the light on the dichroic mirror DM through the focusing lens, wherein the DM is located on the focal plane of the primary LSO imaging system;

C. by using the primary LSO imaging system, providing fundus positioning and navigation for the auxiliary imaging system, and calculating fundus or eyeball motion information obtained from the LSO image by executing a preset closed-loop control algorithm; and D. by applying the closed-loop fundus or eyeball motion information to the orthogonal scanning mirrors of the auxiliary imaging system, corresponding spatial positions of the orthogonal scanning mirrors are adjusted in real time to obtain a tomographic image of the required fundus position.

Among them, the preset closed-loop control algorithm executed in step C is specifically a cross-correlation algorithm, and the fundus or eyeball motion information obtained from the LSO image by executing the cross-correlation algorithm is the fundus or eyeball motion position $(x, y, \theta)$; where $(x, y)$ is a translation amount of fundus motion, and $\theta$ is a rotation amount.

The step D is specifically as: inputting the closed-loop fundus or eyeball motion position information $(x, y, \theta)$ by the primary LSO imaging system into the auxiliary imaging system, and locking the fundus target in the auxiliary imaging system by adjusting the optical scanning position of the scanning mirror in real time; where (x, y) is a translation amount of fundus motion, and θ is a rotation amount.

The present invention is based on the image stabilization method and system of the line scan imaging system (LSO), and has the following beneficial effects:

1) by establishing a closed-loop fundus optical tracking system inside the LSO system, the closed-loop tracking system can be used to control a line scan imaging system, thereby achieving the aim of high-speed, stable and accurate control.

2) the LSO closed-loop control system can be used to obtain the fundus motion signal, and through the pre-calibrated spatial transformation relationship, another one or more optical systems can be controlled to achieve the corresponding fundus target tracking purpose.

3) a frame of image is divided into a plurality of sub-frame elements in a time sequence according to the time sequence of each scan line in each frame image reaching the host system, each sub-frame element containing one or more scan lines. According to the time sequence of each sub-frame element reaching the host system, the fundus motion information contained in each sub-frame element is calculated in real time, and then immediately fed back to a tracking device, such as a high-speed steering mirror and a rotating stage. Through this frequency multiplication technology, the spatial precision and time bandwidth of target tracking may be greatly improved.

DETAILED DESCRIPTION OF THE INVENTION

Hereinafter, the present invention will be further described in detail in connection with the drawings and embodiments of the present invention.

Figure 1:
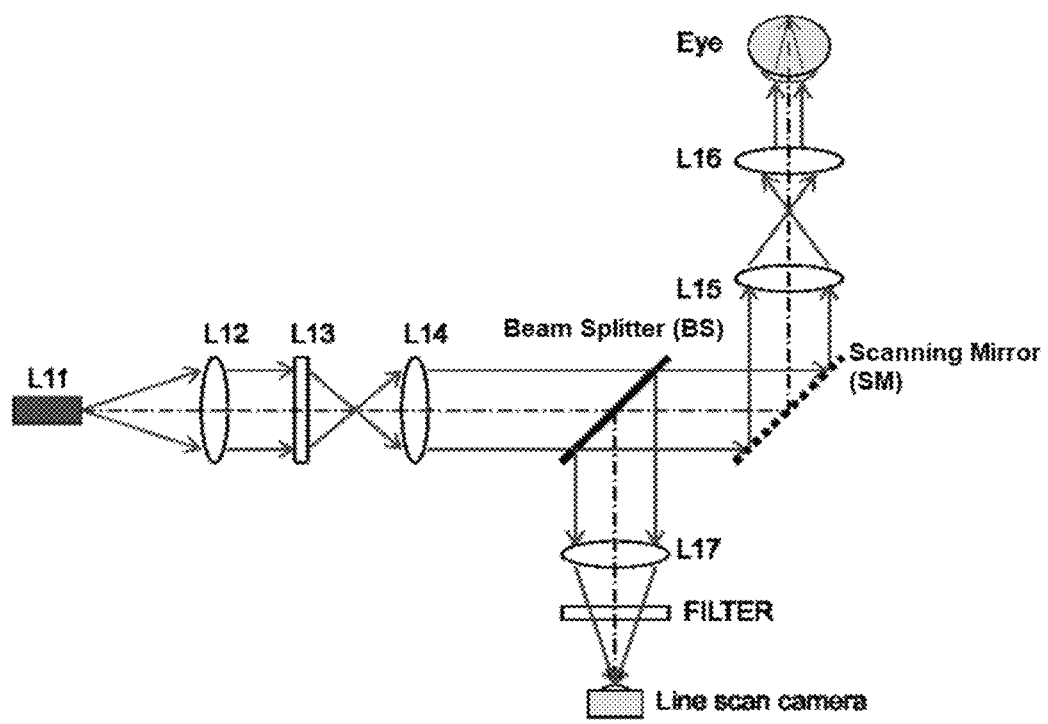
FIG. 1 is a schematic diagram of an optical structure of a conventional line scan fundus camera.

FIG. 1 is a schematic diagram of an optical structure of a conventional line scan fundus camera.

As shown in FIG. 1, a light emitted from a point light source L11 is collimated by a lens L12, and a surface light source is converted into a line light source through a cylinder lens L13, and subsequently relayed to a collimating lens L14. Here, an expansion direction of the line light source in space depends on a mounting direction of the cylinder lens L13 (see FIGS. 9 and 10 for details), and an illumination (expansion) size of the line light source on a fundus depends on the lens L12, lens L13, and lens L14 in a certain extent. A portion of the light emitted by the lens L14 passes through a beam splitter (BS) and reaches a scanning mirror (Steering Mirror or Scanning Mirror, SM); the other portion transmits through the beam splitter (BS) to reach a collimating lens L17, and subsequently reach a line scan camera through a set of filters.

The function of the scanning mirror SM is to generate periodic scanning in the orthogonal direction of the line light source, and the light passes through two collimating zoom lenses L15 and L16 to generate a two-dimensional scanning space at the fundus of eye. A motion trajectory of the scanning mirror (SM) generally presents a sawtooth wave as shown in FIG. 2.

Figure 2:
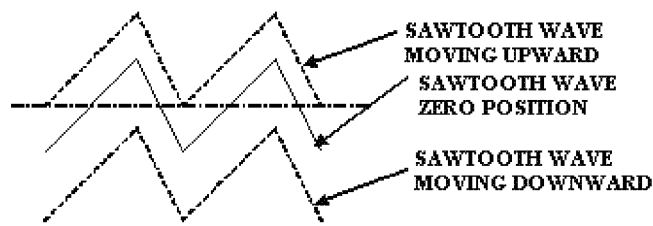
FIG. 2 is a schematic diagram of a sawtooth wave used to control a scanning mirror SM.

FIG. 2 is a schematic diagram of a sawtooth wave used to control a scanning mirror (SM). The frequency of the sawtooth wave determines an image frame rate of the imaging system, and the amplitude of the sawtooth wave determines a size of an optical field of view in the scanning direction.

As shown in FIG. 2, the center of the sawtooth wave is not always at the zero position of the sawtooth wave. The center offset amount of the sawtooth wave actually determines the center position of the scanning field of view. Within a range allowed by an optical design, a user may control the center position of the scanning field of view by adjusting the center offset amount of the sawtooth wave.

Referring to FIG. 1, when the fundus is excited by the light emitted by the point light source L11, the returned signal is reflected from the beam splitter BS to the collimating lens L17 through the same optical path, and then passes through a set of filters to reach the line scan camera. The signal returned from the fundus may be a reflected signal, a fluorescent signal, or other signals; it may also be a variety of other signals that reach the line scan camera simultaneously.

Figure 3:
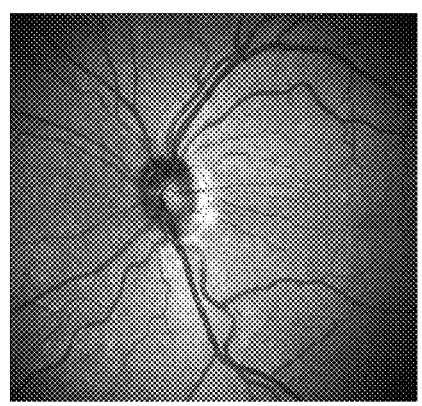
FIG. 3 is a schematic diagram of a fundus image obtained according to the optical system of the line scan fundus camera shown in FIG. 1.

FIG. 3 is a schematic diagram of a fundus image obtained according to the optical system of the line scan fundus camera shown in FIG. 1, that is, a schematic diagram of the fundus image obtained by the line scan fundus camera shown in FIG. 1.

Figure 4:
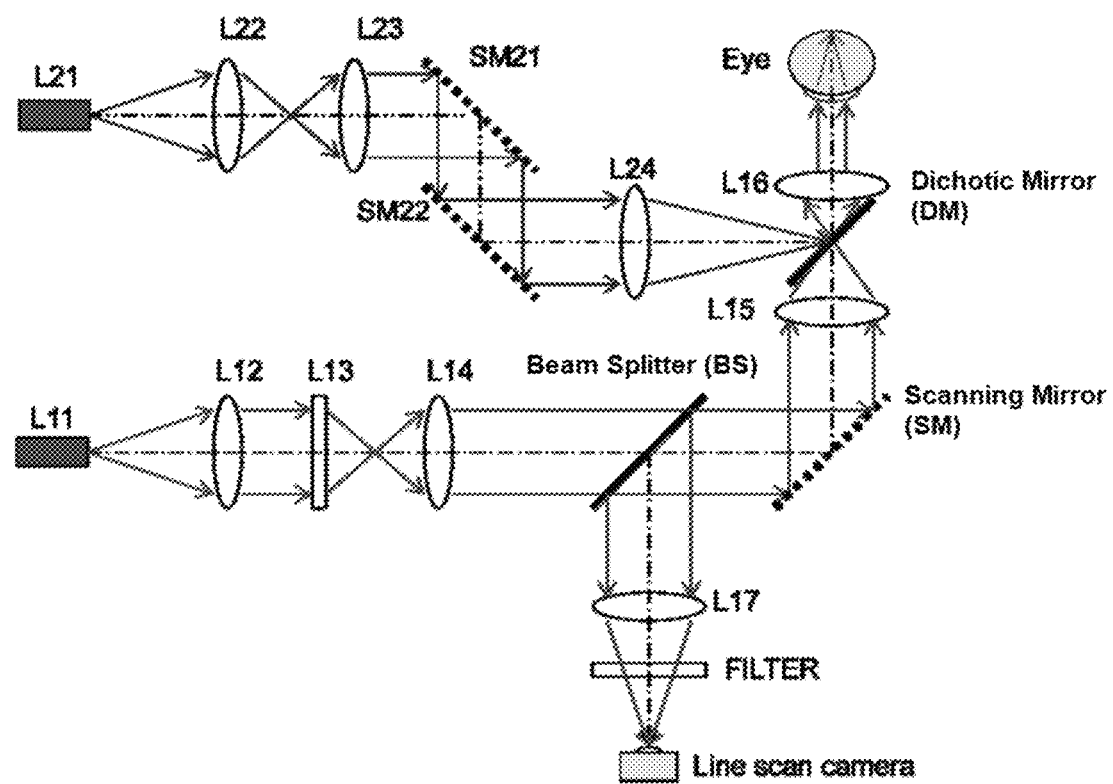
FIG. 4 is a schematic diagram of a conventional line scan imaging system including a primary LSO imaging system without optical tracking and an integrated secondary OCT imaging system.

FIG. 4 is a schematic diagram of a conventional line scan imaging system including a primary LSO imaging system without optical image stabilization (or tracking) and an integrated auxiliary optical coherence tomography (OCT) imaging system.

As shown in FIG. 4, the primary LSO imaging system is the imaging system shown in FIG. 1. Preferably, when the primary LSO imaging system is applied clinically, it may be provided with an auxiliary imaging system customized according to an embodiment of the present invention, such as an OCT product Cirrus of Carl Zeiss. The auxiliary imaging system shown in FIG. 4 is an OCT device.

In the auxiliary imaging system shown in FIG. 4, a light emitted from a second point light source L21 reaches orthogonal scanning mirrors SM21 and SM22 through a collimating system (including collimating lenses L22 and L23), and subsequently is focused on a dichotic mirror DM through a focusing lens L24. The DM is also located on the focal plane of the primary LSO imaging system.

In an embodiment of the present invention, the primary and auxiliary (integrated optical) imaging systems shown in FIG. 4 support simultaneous implementation of two-dimensional fundus reflection (fluorescence) imaging and three-dimensional OCT tomographic imaging.

One function of the primary LSO imaging system is to provide fundus positioning and navigation for the auxiliary imaging system, and to display a corresponding position of the current OCT tomogram in the fundus two-dimensional space to the current user. Another function of the primary LSO imaging system is to calculate completely digital fundus/eyeball motion information (x, y, θ) from the LSO image by performing a preset algorithm. (x, y) is a translation amount of fundus motion, and θ is a rotation amount. Subsequently, (x, y, θ) is applied to the scanning mirrors SM21 and SM22 of the auxiliary imaging system, and the corresponding spatial positions of the scanning mirrors SM21 and SM22 are adjusted in real time to obtain the tomographic image of the required fundus position.

The above-mentioned fundus positioning and navigation process, as well as fundus tracking technology, through the primary LSO image, apply a cross-correlation algorithm or other similar algorithms to calculate a digital fundus motion position (x, y, θ), and accordingly adjust the optical scanning position of the scanning mirrors SM21 and SM22 in real time to lock the fundus target.

The above-mentioned fundus tracking technology has the following characteristics.

Firstly, the primary LSO system obtains only an image similar to FIG. 3 and uses a cross-correlation algorithm or similar algorithms to calculate digital fundus motion information (x, y, θ). The LSO system does not have an optical tracking function. (x, y, θ) is directly calculated from an original image, rather than through the closed-loop control of equation (1) or equation (2).

Secondly, digital fundus tracking only occurs on the scanning mirrors SM21 and SM22 of the auxiliary imaging system, and the primary LSO system does not adjust its own optical parameters to lock the LSO scanning (imaging) position of the fundus accordingly.

Thirdly, the precision and reliability of the digital calculation result (x, y, θ) herein largely depends on various parameters, including a fundus image quality, normal fundus motion, including blinking and saccade and micro saccade. For example, in the cross-correlation algorithm, when a target image (of which the motion amount is to be calculated) drifts out of a reference image, that is, when an eye motion amount is too large, the cross-correlation algorithm cannot obtain accurate fundus motion information, which may lead to a failure of tracking of the auxiliary imaging system.

Figure 5:
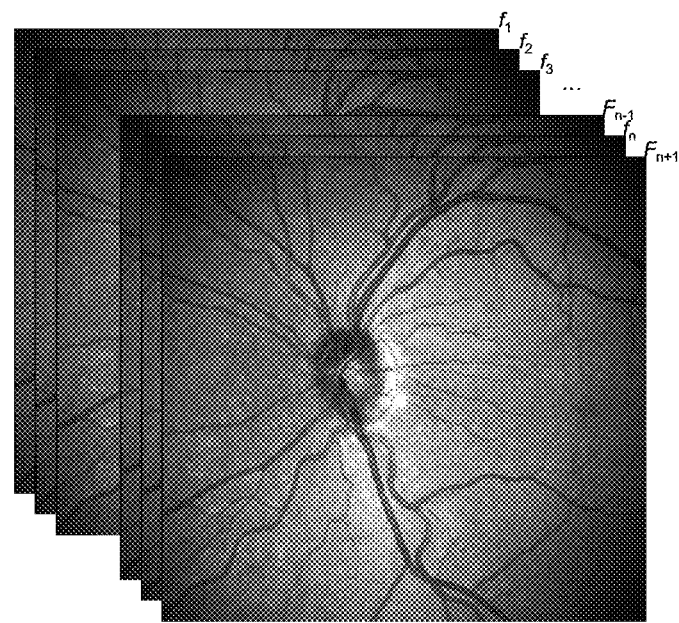
FIG. 5 is a schematic diagram of a fundus motion amount calculated from an image in a unit of frame obtained based on an image stabilization system of a line scan imaging system of the present invention.

Fourthly, the calculation of (x, y, θ) in the prior art is based on a unit of frame, as shown in FIG. 5, which is a schematic diagram of an image obtained by calculating a fundus motion amount from an image in a unit of frame.

Referring to FIG. 5, it is assumed that $f_1$ is the first frame image captured by the LSO, and $f_1$ is used and defined as a "reference frame" image. In a time sequence, the images subsequently obtained by the system are $f_2, f_3, \ldots, f_n, f_{n+1}$, which are defined as "target frame" images.

In the prior art, a software program of the LSO usually starts the cross-correlation algorithm after receiving a complete image frame $f_k$ (k=2, 3, 4, ..., n+1) to calculate a spatial position of $f_k$ relative to $f_1$ ($x_k, y_k, \theta_k$). Once the algorithm program obtains ($x_k, y_k, \theta_k$), it is immediately converted to the scanning mirrors SM21 and SM22 of the auxiliary imaging system through a pre-measured spatial mapping relationship, so that the scanning mirrors SM21 and SM22 are locked at a required fundus scanning position.

However, this frame-based calculation method using ($x_k, y_k, \theta_k$) to control the positions of the scanning mirrors SM21 and SM22 will bring a large spatial error due to a large time delay, that is, a spatial precision of tracking is not high (tens to hundreds of micrometers) and a time response is slow. The reason is in that a typical imaging system outputs 25 to 30 frames of images per second, and thus a time delay carried by each frame of image is already 33 to 40 milliseconds.

For example, a premise for applying the cross-correlation algorithm to calculate the eye motion amount from the image is that the image is needed. As mentioned above, it takes 33-40 milliseconds to acquire a frame of image, in addition to an electronic delay time of converting ($x_k, y_k, \theta_k$) obtained from the algorithm into control signals of the scanning mirror SM21 and SM22 and a mechanical delay of the scanning mirrors SM21 and SM22 in response to the control signals. For a complete control cycle, it is a common phenomenon that the delay time reaches 40-50 milliseconds from the eye motion starting to the scanning mirrors SM21 and SM22 tracking the motion. From the above analysis process, it can be known that among all the factors that may bring delay, the (image) sampling delay of 33 to 40 milliseconds is usually the dominant latency.

Correspondingly, one method for shortening the above-mentioned time delay is to greatly increase a frame rate of image outputting, for example, the LSO outputs 200 frames per second, so that the delay of image sampling may be reduced to 5 milliseconds. However, in order to maintain the same image signal-to-noise ratio in the same imaging field of view, a side effect of the increase of the frame rate of the imaging system is a rapid increase of the nonlinearity of an imaging laser dose. This is not clinically feasible because the use of laser dose is restricted by safety standards.

In summary, the existing LSO imaging systems (products) have deficiencies in optics, electronics, and control, and thus the present invention achieves further improvements and enhancements based on the systems of FIGS. 1 and 4 in terms of optics, electronics, software, and control.

Figure 6:
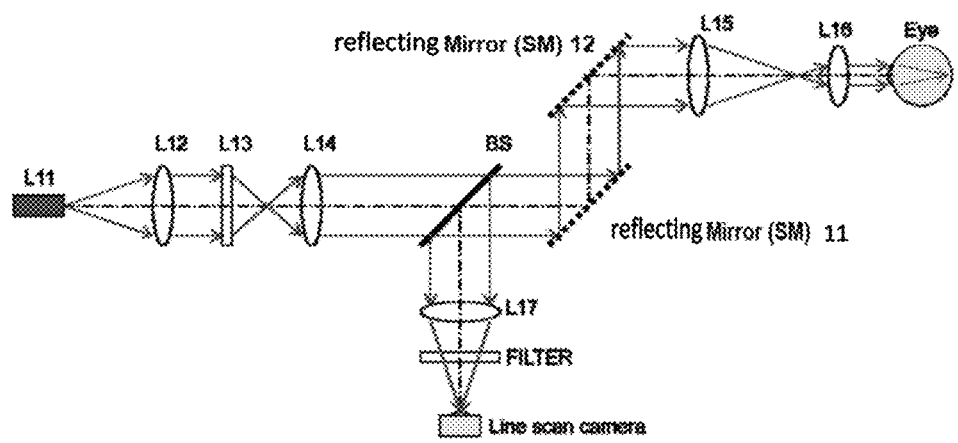
FIG. 6 is a schematic diagram of an improved LSO optical system with internal optical tracking according to an embodiment of the present invention.

FIG. 6 is a schematic diagram of an improved LSO optical system according to an embodiment of the present invention.

As shown in FIG. 6, a second steering mirror is added to the conventional LSO optical system shown in FIG. 1. As another embodiment, the two one-dimensional galvanometers in FIG. 6 may also be replaced with a two-dimensional orthogonal bidirectional vibration microelectronic mechanical systems (MEMS) scanning mirror or other orthogonal scanning mirror structures.

In FIG. 6, the difference from FIG. 1 is in that a steering (reflecting) mirror is added. The mirror (SM) in FIG. 1 is referred as a mirror SM11, and the newly added mirror is referred as a mirror SM12. The operation process of the mirrors SM11 and SM12 is shown in FIG. 7.

Figure 7:
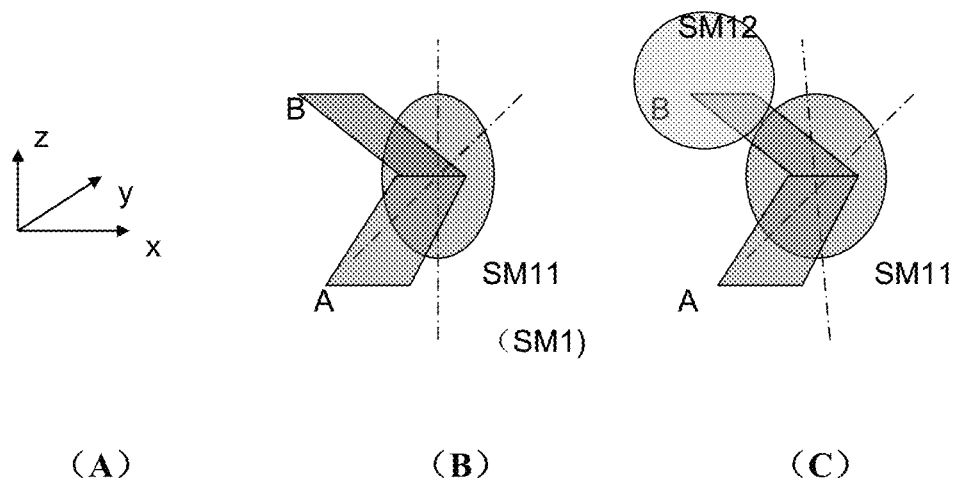
FIG. 7 is a schematic diagram of an operation state of two steering mirrors SM11 and SM12 in the improved LSO optical system shown in FIG. 6.

FIG. 7 is a schematic diagram of an operation state of two steering mirrors SM11 and SM12 in the improved LSO optical system shown in FIG. 6.

For ease of description, firstly a spatial reference coordinate (x, y, z) is defined, as shown in FIG. 7A. When there is only the mirror SM11 (i.e., SM1), referring to FIG. 7B, a line light source A is incident on the mirror SM11. Here, a rotation axis of the mirror SM11 is on the x-axis of the spatial coordinate, so that the mirror SM11 swings on the y-z plane, and thus a two-dimensional scanning surface is generated at the position B. Referring to the conventional LSO shown in FIG. 1, the position B is directly conjugated to an imaging surface of the fundus.

However, in an embodiment of the present invention, after the linear light source from A passes through the mirror SM11, a second steering (reflecting) mirror SM12 is inserted at the position B in FIG. 7C. Following the above definition, here the rotation axis of the mirror SM12 is on the z-axis and swings in the x-y plane.

It is understood that the reference coordinate (x, y, z) in FIG. 7A may be defined arbitrarily, as long as the motion axis of the mirror SM11 and the motion axis of the mirror SM12 are orthogonal.

The operation mode of the double mirrors may be realized by the double mirrors structure shown in FIG. 6, such as using two one-dimensional 6210H galvanometer or 6220H galvanometer of Cambridge Technology; may also be realized by a steering mirror provided with two independent orthogonal motion axes, such as using a S-335.2SH fast tip/tilt mirror of PI.

The function and effect of using the mirrors SM11 and SM12 in combination as shown in FIGS. 6 and 7 is in that a scanning surface generated on the fundus of the LSO may be adjusted to any position in a 360-degree space by changing offset amounts of the mirrors SM11 and SM12 within an allowable range of the optical system. This will be further described in FIG. 8 below.

Figure 8:
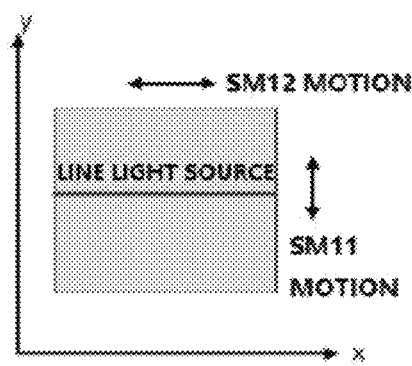
FIG. 8 is a schematic diagram of adjusting a position state of an imaging surface in a 360-degree space by changing offset amounts of the mirrors SM11 and SM12.

FIG. 8 is a schematic diagram of adjusting a position state of an imaging surface in a 360-degree space by changing offset amounts of the mirrors SM11 and SM12.

As shown in FIG. 8, a parameter for controlling the mirror SM12 is a translation amount in a simple situation (referring to FIG. 9 below for a complex control situation), so as to adjust a position of the imaging surface in a horizontal direction, which may be used to track the target motion in the horizontal direction. Here, there are generally a plurality of parameters for controlling the mirror SM11. On one hand, the mirror SM11 is used for scanning, and on the other hand, used for translation or target tracking of the imaging surface in a vertical direction (referring to FIG. 2).

Figure 11:
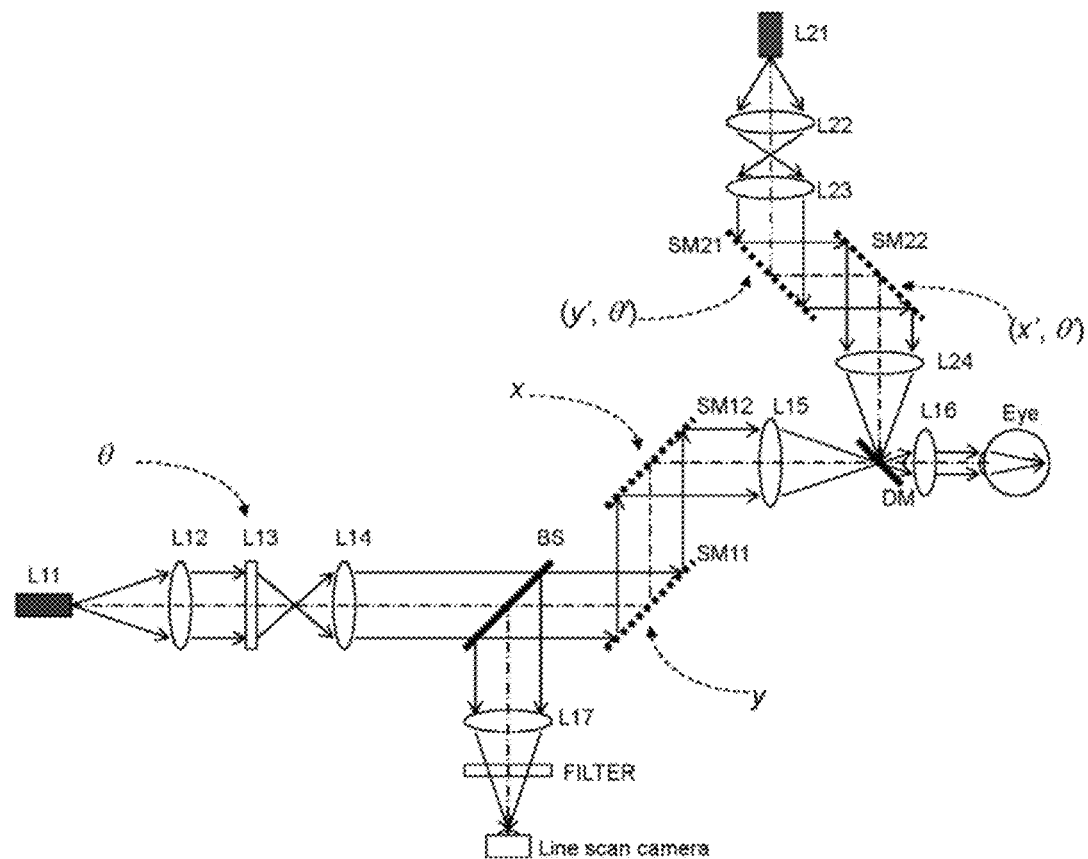
FIG. 11 is a principal schematic diagram of a primary LSO imaging system with closed-loop optical tracking integrated with another auxiliary imaging system according to an embodiment of the present invention.

Combining the functions of the mirrors SM11 and SM12 in connection with an intelligent control algorithm, the LSO optical system may implement a fundus optical tracking inside the LSO while scanning the two-dimensional fundus. FIG. 11 below is referred for related control and algorithm implementation.

In summary, FIG. 6 constructs a complete closed-loop control system. A light from the point light source L11 reaches the fundus through the mirrors SM11 and SM12, which is a two-dimensional scanning space. A signal returned from the space where the fundus is scanned is scanned by the mirrors SM11 and SM12 again to reach a photodetector, which is a line scan camera for recording the image signal returned from the fundus.

In addition, the reason that FIG. 6 of the present invention constructs a complete closed-loop control system is in that after the fundus tracking system is activated, the system has a following equation:

$$(x_{t+1}, y_{t+1}) = (x_t, y_t) + g(\Delta x_t, \Delta y_t) \quad (1)$$

In the above equation (1), $(x_t, y_t)$ represents control instructions on the mirrors SM11 and SM12 at the current sampling time point (equivalent to their respective motion offset amounts), $(\Delta x_t, \Delta y_t)$ represents a relative motion amount of an image (target frame) recorded by the line scan camera to the reference image (reference frame), g represents a gain of the closed-loop control system, and $(x_t+t, y_t+t)$ represents the next new set of instructions applied to the mirrors SM11 and SM12 by the existing signals (equivalent to the motion offset amounts).

Since before entering the photodetector (the line scan camera herein), the motion signal from the fundus has been optically compensated by the mirrors SM11 and SM12, the motion signal obtained from the photodetector is always a residual motion signal, which is $(\Delta x_t, \Delta y_t)$ in equation (1).

The closed-loop control described above can also compensate for a rotation signal of the eyeball. One method is to mount the cylinder lens L13 generating the line light source in FIG. 6 and the coupled line scan camera on a 360-degree controllable rotating bracket, so that a line-expanded light source may be rotated at any position in the 360-degree space (referring to FIG. 9).

Figure 9:
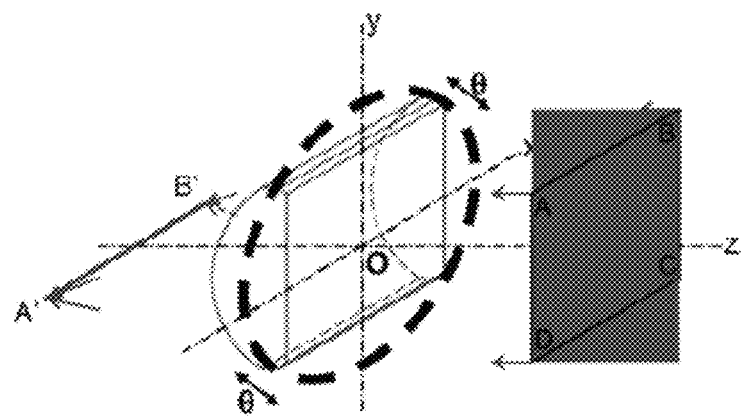
FIG. 9 is a schematic diagram of a position of a line light source generated by a rotation device for rotating a cylinder lens L13 and a line scan camera coupled thereto in a 360-degree space.

FIG. 9 is a schematic diagram of a position of a line light source generated by a rotating device for rotating the cylinder lens L13 in the 360-degree space.

As shown in FIG. 9, the axis of the cylinder lens and the coupled line scan camera (for simplicity, the line scan camera is not shown in FIG. 9) are mounted on a controllable rotating mechanism (shown by a thick dashed line) at the origin position O of the coordinates, and may be rotated freely within 360 degrees of the x-y plane. The optical axis of the optical system is in the z direction shown in FIG. 9. The plane light source ABCD coming from the right side shown in FIG. 9 is focused into a linear light source NB' through a cylinder lens. The cylinder lens may also be mounted on any rotating mechanism to generate the linear light source A'B' in any direction.

Figure 10:
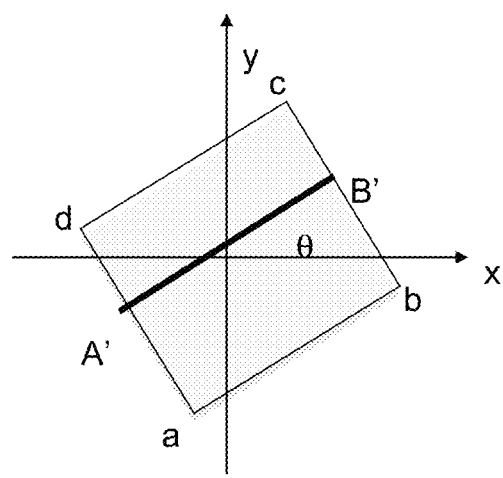
FIG. 10 is a schematic diagram of a state of a line light source with an arbitrary rotation angle generated by rotating a cylinder lens and a related scanning surface.

The rotating device shown in FIG. 9 may be rotated to adjust a projection direction of the line light source A'B' on the x-y plane, and the angle between A'B' and the x axis is consistent with the rotation angle of the rotating device, that is θ (refer to the FIG. 10).

FIG. 10 is a schematic diagram of a state of a linear light source with an arbitrary rotation angle generated by rotating a cylinder lens and a related scanning surface.

As shown in FIG. 10, a scanning surface abcd as shown in the figure is generated from the line light source A'B'. At this time, both the scanning (reflecting) mirrors SM11 and SM12 of FIG. 6 have to participate in the scanning, instead of only the scanning (reflecting) mirror SM11 shown in FIG. 8 participating in scanning.

A technical implementation of the scanning (reflecting) mirrors SM11 and SM12 participating in the scanning process at the same time is using the sawtooth wave shown in FIG. 2 as a driving signal basis of SM11 and SM12, and then multiplying an amplitude of each scanning (reflecting) mirror by the respective basis signal according to the rotation angle of FIG. 10. As defined in FIG. 8 and shown in FIG. 10, the amplitude obtained by the scanning basis of the scanning (reflecting) mirror SM11 is (A'B'/2)sin(θ), and the amplitude obtained by the scanning basis of the scanning (reflecting) mirror SM12 is (A'B'/2)cos(θ). It should be pointed out that the definition of the scanning direction and rotation direction is arbitrary.

In this case, the relationship equation (1) may be updated to, $$(x_{t+1}, y_{t+1}, \theta_{t+1}) = (x_t, y_t, \theta_t) + g(\Delta x_t, \Delta y_t, \Delta \theta_t) \quad (2)$$

Herein, $\theta_t$ is an angle applied by the closed-loop control system on the rotating bracket; $(x_t, y_t)$ is translational amounts applied on the scanning (reflecting) mirrors SM11 and SM12, and meanwhile, $(x_t, y_t)$ is also translation amounts superimposed on scan signals of FIG. 10 generated by the respective scanning (reflecting) mirrors SM11 and SM12. In the same way, in the above equation (2), $(x_t, y_t, \theta_t)$ is the control instructions on the mirrors SM11, SM12, cylinder lens and line scan camera rotating bracket at the current sampling time point (equivalent to their respective motion offset amounts); $(\Delta x_t, \Delta y_t, \Delta \theta_t)$ is the relative motion amounts of the image (target frame) recorded by the line scan camera to the reference image (reference frame); g is the gain of the closed-loop control system; $(x_{t+1}, y_{t+1}, \theta_{t+1})$ is the next new set of instructions applied to mirrors SM11, SM12, cylinder lens and line scan camera rotation bracket (equivalent to motion offset amount and rotation angle).

The primary LSO imaging system of the present invention in the above embodiments of FIGS. 6-10 integrates an internal fundus optical tracking closed-loop control system, such as the control mode of equation (1) or equation (2). On this basis, the auxiliary imaging system as shown in FIG. 4 is added. The auxiliary imaging system may be an OCT system, or may be used for other purposes, such as a single-point or multi-point target strike fundus laser treatment system. The specific technical implementation of these two parts is described in detail in another patent application.

FIG. 11 is a principal schematic diagram of a primary LSO imaging system with closed-loop optical tracking integrated with another auxiliary imaging system according to an embodiment of the present invention.

As shown in FIG. 11, the primary LSO imaging system on the left side integrates another auxiliary imaging system in the upper part, in which the closed-loop optical tracking device of the primary LSO imaging system on the left side performs closed-loop optical tracking by preforming a preset closed-loop control algorithm to calculate the fundus or eyeball motion information obtained from the LSO image. The closed-loop optical tracking device mainly includes a second scanning mirror (SM11), a first scanning mirror (SM12) and a cylinder lens (L13). The closed-loop optical tracking device is used to calculate the fundus or eyeball motion information obtained from the LSO image, that is, the control signal, according to the preset closed-loop control algorithm, so as to realize the closed-loop optical tracking function.

The auxiliary imaging system in the upper part passes the light emitted by the point light source L21 through a collimating system (including the collimating lenses L22 and L23) to the orthogonal scanning mirrors SM21 and SM22, then focuses the light on the dichroic mirror (DM) through the focusing lens L24, and then make the light reach the fundus of the eye through the divergent lens L16. The DM is located on the focal plane of the primary LSO imaging system. By applying the closed-loop fundus or eyeball motion information, that is, control signals (x', y', θ') to the orthogonal scanning mirrors of the auxiliary imaging system, corresponding spatial positions of the orthogonal scanning mirrors are adjusted in real time to obtain a tomographic image of the required fundus position or a fundus single point or array strike target.

The operation principle thereof is in that the control signal (x, y, θ) is applied to the second scanning (reflecting) mirror SM11, the first scanning (reflecting) mirror SM12 and the cylinder lens L13 (preferably also including the rotating bracket of the line scan camera) of the primary LSO imaging system. The parameters of the control signal are as shown by the dashed lines with arrows, which come from the closed-loop control system inside the LSO, and the parameters thereof are consistent with those in equations (1) and (2). Compared with pure digital motion signals of the conventional LSO system, this group of closed-loop control motion signals has the following advantages: 1) smooth; 2) stable; 3) strong anti-interference.

In FIG. 11, the control signal (x', y', θ') applied to the scanning (reflecting) mirrors SM21 and SM22 of the auxiliary imaging system completely inherit the advantages of the above-mentioned closed-loop control signals (x, y, θ), as (x', y', θ') is obtained by a spatial transformation of (x, y, θ), as shown in equation (3):

$$(x', y', \theta') = f(x', y', \theta'; x, y, \theta)(x, y, \theta) \quad (3)$$

The spatial transformation relation f(x', y', θ'; x, y, θ) of equation (3) is completely determined by the parameters of the optical system. In equation (3), the spatial transformation relationship f(x', y', θ'; x, y, θ) from the primary LSO imaging system to the auxiliary LSO imaging system is measured quickly, efficiently, accurately, and fully automatically, which is not described in detain here.

FIGS. 6-11 above describe the optical and mechanical implementation of the present invention. The following describes the control implementation part of the embodiment of the present invention, focusing on how to calculate and obtain the fundus position at a high speed through an algorithm, so as to quickly adjust the scanning (reflecting) mirrors SM11 and SM12, and the scanning (reflecting) mirrors SM21 and SM22 to realize fundus tracking with high spatial precision and low time delay.

Referring to FIG. 5, the existing data processing technology calculates fundus motion from the LSO image in a unit of frame. In an embodiment of the invention, the frequency multiplication technology is used for calculation.

Figure 12:
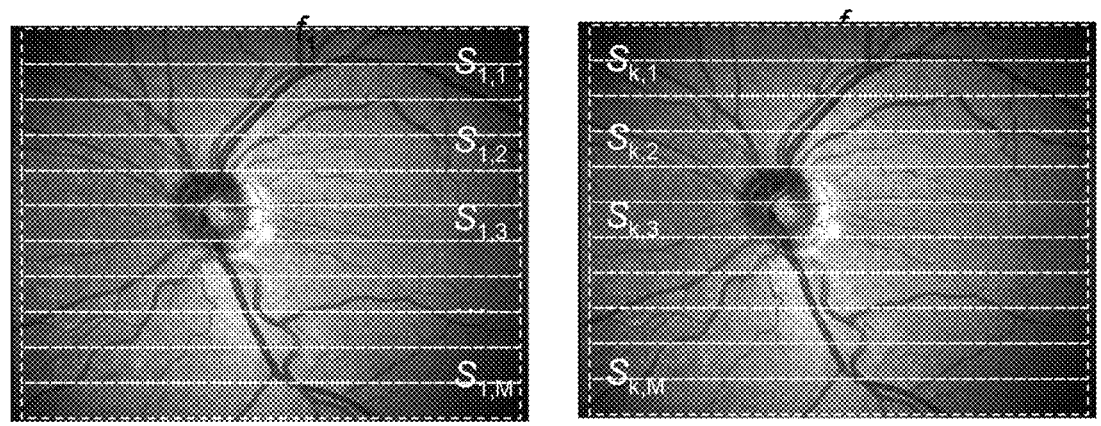
FIG. 12 is a schematic diagram of reducing a time delay of fundus calculation using frequency multiplication technology according to an embodiment of the present invention.

FIG. 12 is a schematic diagram of reducing a time delay of fundus calculation using frequency multiplication technology according to an embodiment of the present invention.

As shown in FIG. 12, the image on the left side, that is, f1 in FIG. 12A is consistent with f1 in FIG. 5, and is still used as a reference frame. The image on the right side, i.e., $f_k$ in FIG. 12B is any frame image (k>1) of a target frame. In the present invention, each frame image is divided into a plurality of equally spaced sub-frame elements in a time sequence according to data reached by the scanning camera, for the convenience of calculation, such as $S_{1,1}$, $S_{1,2}$, $S_{1,3}$, ..., $S_{1,M}$. $S_{1,1}$, $S_{1,2}$, $S_{1,3}$, ..., $S_{1,M}$, which are all M sub-frame elements in the reference frame, and $S_{k,1}$, $S_{k,2}$, $S_{k,3}$, ..., $S_{k,M}$ are all M sub-frame elements in the k-th target frame.

Here, the method of the present invention is to divide any frame of image into a plurality of equally spaced sub-frame elements the scanning direction of SM11 (as described above, normally SM11 and SM12 shown in FIG. 10 are combined. For convenience, only SM11 shown in FIG. 8 is used as a reference here, and the following description is the same). The equal spacing means that each sub-frame element contains the same number of scan lines.

FIGS. 12A and 12B show elongated sub-frame elements in the horizontal direction, indicating that SM11 scans in the vertical direction. As shown in FIG. 10, the combination of SM11 and SM12 allows the optical system to scan in any direction in the 360-degree space, thus the dividing of sub-frame elements in FIG. 12 needs to be adjusted to the corresponding orthogonal direction. For convenience, FIG. 2 is referred to for the scan signal of SM11, and FIG. 13 is referred for the dividing manner of the sub-frame elements.

Figure 13:
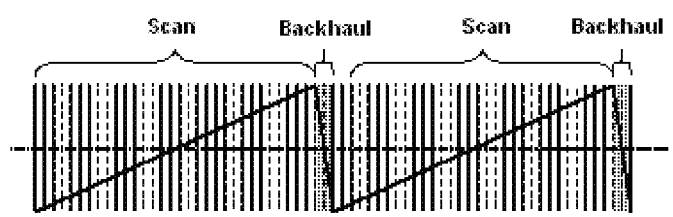
FIG. 13 is a schematic diagram of a dividing manner of a scan signal of a scanning (reflecting) mirror SM11 and a sub-frame element.

FIG. 13 is a schematic diagram of a dividing manner of a scan signal of a scanning (reflecting) mirror SM11 and a sub-frame element.

As shown in FIG. 13, the vertical dash line represents the time (equivalent spatial) position of each sub-frame element; the thick solid line represents the sawtooth wave that drives SM11 (or the combination of SM11 and SM12, consistent with the context) to scan. Normally, the sawtooth wave has a scan section and a backhaul section, as shown in FIG. 13. In an extreme case, the time in the backhaul section is 0, then the sawtooth wave becomes a triangle wave. In an implementation, a triangular wave may also be used instead of the sawtooth wave as the scan signal of SM11, as long as the scanning mirrors SM11 and SM12 are not damaged.

In another embodiment of the present invention, a line scan camera (OCTOPLUS3) of Wasatch Photonics is used, and the camera receives a 16 kHz trigger signal. That is, the camera is set to receive 16,000 line signals per second. In an embodiment, the 16 kHz trigger clock is generated from a Xilinx FPGA (SP605), or it can be generated from other chips such as DSP.

In an embodiment of the present invention of the LSO system, each scan cycle of the SM11 includes 544 lines, of which 512 lines are in the scan section and 32 lines are in the backhaul section. Thus, the frame rate of the image is:

*fps*=16000/544=29.4

The 512 lines of the scan section are used for imaging, that is, the image shown in FIG. 12. The data in the backhaul section is automatically discarded by the system.

The above dividing manner is only one embodiment of the present invention, and different systems may have completely different dividing manners.

In the case shown in the above embodiment, in this embodiment, a complete scan cycle of SM11 is divided into 32 (scan)+2 (backhaul) sub-sections, and each sub-section contains 16 scan lines (or time units). As shown by the vertical dashed line in FIG. 13, such a complete cycle is exactly 34×16=544 lines.

The key point of the embodiment of the present invention is in that once 16 lines reach the camera, that is, data of one sub-frame element is prepared, the data of the sub-frame element is immediately sent from the camera to the host PC or other computing units, such as CPU, GPU, DSP, FPGA, etc.; the processing unit in the embodiment of the present invention employs a graphics processor GTX1050 of nVidia. The sub-frame element data of the 16 lines corresponds to one position of $S_{k,1}$, $S_{k,2}$, $S_{k,3}$, ..., $S_{k,M}$ in FIG. 12. Obviously, in this example, M=32, that is, a total number of sub-frame elements in each frame image.

Once the calculation unit receives data of the latest sub-frame element, an algorithm such as the cross correlation algorithm immediately starts to calculate the position of the sub-frame element relative to the reference frame. Normally, it is to find a relative position of the sub-frame element $S_{k,m}$ of the target frame to the sub-frame element $S_{1,m}$ of the reference frame. However, it may also be to find a relative position of the sub-frame element $S_{k,m}$ of the target frame to other sub-frame element $S_{1,p}$ ($p \neq m$) of the reference frame. The above-mentioned specific algorithm implementing process is disclosed in U.S. Pat. No. 9,406,133.

The advantage of using this method is in that the time to obtain a sub-frame element $S_{k,m}$ only requires:

16/16000=1 millisecond;

instead of waiting for a full frame:

544/16000=34 milliseconds.

After transplanting the cross correlation algorithm from CPU to nVidia GPU (GTX1050), the time from receiving the data of the sub-frame element $S_{k,m}$ to transmitting the motion signal to SM11 and SM12 plus the mechanical response time of SM11 and SM12 is less than 2 milliseconds. This is equivalent to reducing the total delay time of one control cycle from (34+2)=36 milliseconds that can be achieved by the best existing device to (1+2)=3 milliseconds, the latter being 1/12 of the former.

The frequency by which the best existing device adjusts SM11 (without SM12) is 29.4 Hz of the frame rate of image, and the frequency by which the device of the present invention adjusts the SM11 and SM12 is 1000 Hz of the sampling time of the sub-frame elements. This is the frequency multiplication technique described above. Similarly, the specific numbers here are only an example in the invention, and different systems and different applications can use different parameters to achieve the above-mentioned frequency multiplication technology.

Compared with the best existing technology, the present invention employs the technology of transplanting the cross correlation algorithm from the CPU to the nVidia GPU (GTX1050), which brings the advantage of increasing the spatial precision and 3 dB time bandwidth of the tracking system by more than an order of magnitude.

Figure 14:
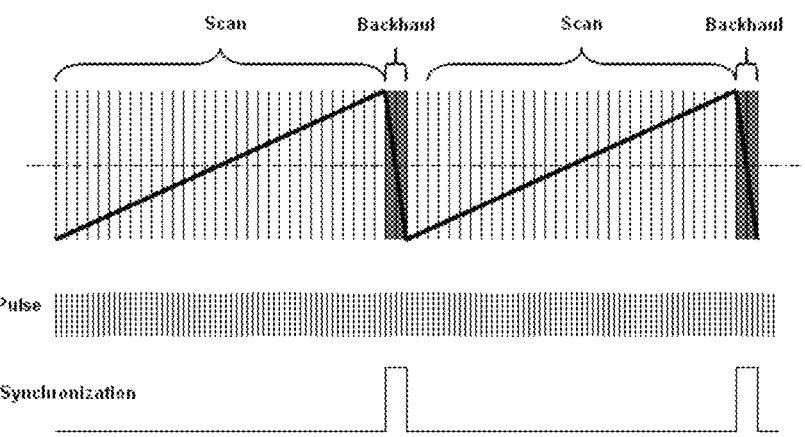
FIG. 14 is a schematic diagram of a scan signal and a synchronization signal of a line scan system.

Continuing to apply the above example, the data sampling of the sub-frame element of the line scan system may be gradually realized by the following method (refer to FIG. 14).

FIG. 14 is a schematic diagram of a scan signal and a synchronization signal of a line scan system.

As shown in FIG. 14, the 16 kHz line pulse is a system reference clock generated by an FPGA. The scan signal in FIG. 13 (that is, the upper part of FIG. 14) and the 29.4 Hz frame synchronization signal in the lower part of FIG. 14 are obtained by phase-locking from a 16 kHz reference pulse. In addition, the scan signal and the frame synchronization signal are also completely synchronized. During the scan signal rising period, the frame synchronization signal is at a low level; during the scan signal falling period, the frame synchronization signal is at a high level. The generation of these signals can be implemented on an FPGA or DSP or other electronic hardware. In an embodiment of the present invention, an FPGA development board SP605 (Spartan 6 chip) of Xilinx is used.

Normally, a data output mode of the line scan camera is controlled by a user inputting a trigger signal of the line scan camera. This trigger signal has to include both the 16 kHz reference pulse of FIG. 14 and the frame synchronization signal of FIG. 14, that is a combination of them, as shown in FIG. 15, which is the synchronization trigger signal required by the line scan camera OCTOPLUS3 of Wasatch Photonics described above.

Figure 15:
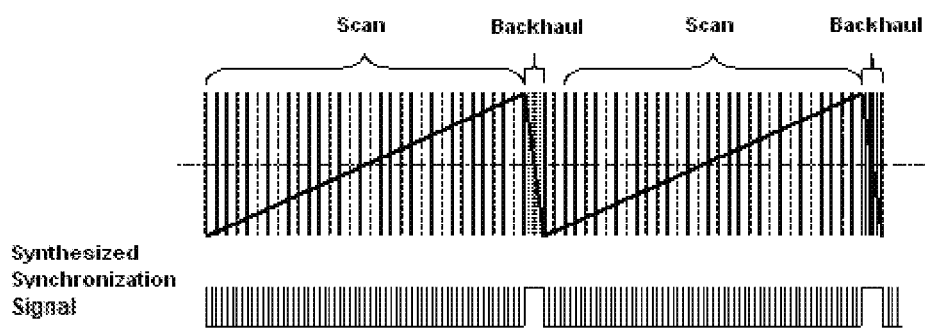
FIG. 15 is a signal that combines a line reference clock and a frame synchronization signal to trigger a line scan camera.

As shown in FIG. 15, it shows a signal that combines the line reference clock and the frame synchronization signal for triggering the line scan camera, but the standard method shown in FIG. 15 cannot trigger the line scan camera to send the data of the sub-frame element of 1000 Hz. Only using the 16 kHz reference clock in FIG. 14, it is impossible to guarantee the synchronization of the received image and the scan signal. In order to obtain the sub-frame image of 1000 Hz synchronized with the scan signal, the existing trigger technology is also appropriately improved in an embodiment of the present invention.

The trigger signal of the line scan camera uses only the 16 kHz reference clock in FIG. 14, and the buffer size is 16 lines. This means that the line scan camera has nothing to do with the frame synchronization status, once the line scan camera receives data of 16 lines, it immediately sends the same to the PC. However, an embodiment of the present invention makes an additional synchronization in hardware implementation.

Any camera has states of starting and ending data sampling. Once the user clicks on a software interface to start sampling, the 16 kHz reference clock transmitted to the line scan camera does not start immediately, but waits until a rising or falling edge of the frame synchronization signal to trigger the 16 kHz reference clock of the line scan camera. When implementing this function on FPGA in an embodiment of the present invention, the following Verilog code is used:

```
always @ (posedge v_sync) begin
  if (camera_start == 1'b0)
    camera_trigger <= 1'b0;
  else
    camera_trigger <= line_trigger_16kHz;
end
```

In the above FPGA code, v_sync is the frame synchronization signal of 29.4 Hz shown in FIG. 14, camera_start is a status register for the user to turn on and off the camera, and camera_trigger is a trigger clock sent to the line scan camera. The code example is a rising edge trigger of v_sync (posedge v_sync), and the other case is a falling edge trigger (negedge v_sync). Only when the rising edge (or falling edge) of _sync and camera_start occur at the same time, the 16 kHz reference clock is sent to the line scan camera, otherwise, the line scan camera always obtains a low level and is in a sampling waiting state. The sampling here is defined as sending image data from the camera to a receiving device, such as a PC, GPU, DSP, or other devices.

The difference between rising edge trigger and falling edge trigger is as shown in FIG. 14. When it is triggered at the rising edge, the first and second units of every 34 sub-frame elements are the data in the backhaul section and need to be eliminated. When it is triggered at the falling edge, the 33rd and 34th units of every 34 sub-frame elements are the data in the backhaul section and need to be eliminated.

The specific numbers described in the above embodiments are only one parameter setting of various embodiments of the present invention, and different systems and different application scenarios can use different parameters. For example, the scan section may be 1024 lines, and the backhaul section is 32 lines, thus the frame rate of the system becomes 16000/(1024+32)=15.2 Hz. In addition, according to the parameters of the line scan camera, the frequency of the reference line clock may also be adjusted from 16 kHz to 20 kHz or down to 15 kHz, etc., which are all parameters that may be changed.

The size of the sub-frame element may also be adjusted. For example, the above 1000 Hz may be changed to 500 Hz, and each sub-frame element has 32 lines. It may also be other sub-frame sampling frequency.

The foregoing description is only preferred embodiments of the present invention, and are not used to limit the protection scope of the present invention.

The invention claimed is:

1. An image stabilization method based on a line scan imaging system, comprising the following steps:
    (A) adding an auxiliary imaging system controlled by a primary LSO imaging system with internal closed-loop optical tracking to the primary LSO imaging system;
    (B) using the auxiliary imaging system, passing a light emitted by a point light source through a collimating system to an orthogonal scanning mirror, then focusing the light on a dichroic mirror (DM) through a focusing lens, wherein the DM is located on a focal plane of the primary LSO imaging system;
    (C) by using the primary LSO imaging system, providing fundus positioning and navigation for the auxiliary imaging system, and calculating fundus or eyeball motion information obtained from an LSO image by executing a preset closed-loop control algorithm; and
    (D) by applying a closed-loop fundus or eyeball motion information to the orthogonal scanning mirror of the auxiliary imaging system, corresponding spatial positions of the orthogonal scanning mirror are adjusted in real time to obtain a tomographic image of a required fundus position;
    wherein the preset closed-loop control algorithm executed in step C is specifically a cross-correlation algorithm, and the closed-loop fundus or eyeball motion information obtained from the LSO image by executing the cross-correlation algorithm is a fundus or eyeball motion position (x, y, θ); where (x, y) is a translation amount of fundus motion, and θ is a rotation amount.

2. The image stabilization method based on the line scan imaging system according to claim 1,
    wherein the primary LSO imaging system is used for self-imaging and provides fundus positioning and navigation for the auxiliary imaging system, and calculates the closed-loop fundus or eyeball motion information obtained from the LSO image by executing the preset closed-loop control algorithm to perform the closed-loop optical tracking;
    wherein the auxiliary imaging system passes the light emitted by the point light source through the collimating system to the orthogonal scanning mirror, then focuses the light on the DM through the focusing lens, the DM is located on the focal plane of the primary LSO imaging system; by applying the closed-loop fundus or eyeball motion information to the orthogonal scanning mirror of the auxiliary imaging system, the corresponding spatial positions of the orthogonal scanning mirror are adjusted in real time to obtain the tomographic image of the required fundus position or a fundus single point or array strike target.

3. The image stabilization method based on the line scan imaging system according to claim 1, wherein a closed-loop optical tracking device of the primary LSO imaging system includes a second scanning mirror (SM11), a first scanning mirror (SM12) and a cylinder lens (L13), which is used to calculate the closed-loop fundus or eyeball motion information obtained from the LSO image, that is, a control signal, according to the preset closed-loop control algorithm, to realize a closed-loop optical tracking function.

4. The image stabilization method based on the line scan imaging system according to claim 3, wherein the closed-loop optical tracking device of the primary LSO imaging system further comprises a line scan camera and a rotating bracket for the line scan camera.

5. The image stabilization method based on the line scan imaging system according to claim 1, wherein the auxiliary imaging system is an auxiliary optical coherence tomography OCT imaging system, or a fundus single point or array target strike imaging system.

6. The image stabilization method based on the line scan imaging system according to the claim 1, wherein the auxiliary imaging system further comprises the point light source, and the light emitted by the point light source passes through the collimating system before reaching the orthogonal scanning mirror, and wherein the collimating system comprises a plurality of collimating lenses.

7. An image stabilization method based on a line scan imaging system, comprising the following steps:
(A) adding an auxiliary imaging system controlled by a primary LSO imaging system with internal closed-loop optical tracking to the primary LSO imaging system;
(B) using the auxiliary imaging system, passing a light emitted by a point light source through a collimating system to an orthogonal scanning mirror, then focusing the light on a dichroic mirror (DM) through a focusing lens, wherein the DM is located on a focal plane of the primary LSO imaging system;
(C) by using the primary LSO imaging system, providing fundus positioning and navigation for the auxiliary imaging system, and calculating fundus or eyeball motion position information (x, y, θ) obtained from an LSO image by executing a preset closed-loop control algorithm; and
(D) by applying a closed-loop fundus or eyeball motion position information (x, y, θ) to the orthogonal scanning mirror of the auxiliary imaging system, corresponding spatial positions of the orthogonal scanning mirror are adjusted in real time to obtain a tomographic image of a required fundus position;
wherein step D is specifically as: inputting the closed-loop fundus or eyeball motion position information (x, y, θ) by the primary LSO imaging system into the auxiliary imaging system, and locking a fundus target in the auxiliary imaging system by adjusting a optical scanning position of the orthogonal scanning mirror in real time; where (x, y) is a translation amount of fundus motion, and θ is a rotation amount.

8. The image stabilization method based on the line scan imaging system according to claim 7, wherein the primary LSO imaging system is used for self-imaging and provides fundus positioning and navigation for the auxiliary imaging system, and calculates the closed-loop fundus or eyeball motion position information (x, y, θ) obtained from the LSO image by executing the preset closed-loop control algorithm to perform the closed-loop optical tracking;
wherein the auxiliary imaging system passes the light emitted by the point light source through the collimating system to the orthogonal scanning mirror, then focuses the light on the DM through the focusing lens, the DM is located on the focal plane of the primary LSO imaging system; by applying the closed-loop fundus or eyeball motion position information (x, y, θ) to the orthogonal scanning mirror of the auxiliary imaging system, the corresponding spatial positions of the orthogonal scanning mirror are adjusted in real time to obtain the tomographic image of the required fundus position or a fundus single point or array strike target.

9. The image stabilization method based on the line scan imaging system according to claim 7, wherein a closed-loop optical tracking device of the primary LSO imaging system includes a second scanning mirror (SM11), a first scanning mirror (SM12) and a cylinder lens (L13), which is used to calculate the closed-loop fundus or eyeball motion position information (x, y, θ) obtained from the LSO image, that is, a control signal, according to the preset closed-loop control algorithm, to realize a closed-loop optical tracking function.

10. The image stabilization method based on the line scan imaging system according to claim 9, wherein the closed-loop optical tracking device of the primary LSO imaging system further comprises a line scan camera and a rotating bracket for the line scan camera.

11. The image stabilization method based on the line scan imaging system according to claim 7, wherein the auxiliary imaging system is an auxiliary optical coherence tomography OCT imaging system, or a fundus single point or array target strike imaging system.

12. The image stabilization method based on the line scan imaging system according to claim 7, wherein the auxiliary imaging system further comprises the point light source, and the light emitted by the point light source passes through the collimating system before reaching the orthogonal scanning mirror, and wherein the collimating system comprises a plurality of collimating lenses.

\* \* \* \* \*